(12) United States Patent
Nin et al.

(10) Patent No.: US 12,268,887 B2
(45) Date of Patent: *Apr. 8, 2025

(54) METHOD OF ESTABLISHING A COMMUNICATION SESSION BETWEEN AN EXTERNAL DEVICE AND AN IMPLANTABLE MEDICAL DEVICE

(71) Applicant: Greatbatch Ltd., Clarence, NY (US)

(72) Inventors: Federico Nin, Montevideo (UY); Andres Duarte, Montevideo (UY); Andres Casaravilla, Montevideo (UY); Juan Andres da Misa, Montevideo (UY); Cecilia Eluen, Montevideo (UY); Oscar Sanz, Montevideo (UY)

(73) Assignee: Greatbatch Ltd., Clarence, NY (US)

( * ) Notice: Subject to any disclaimer, the term of this patent is extended or adjusted under 35 U.S.C. 154(b) by 150 days.

This patent is subject to a terminal disclaimer.

(21) Appl. No.: 18/115,868

(22) Filed: Mar. 1, 2023

(65) Prior Publication Data

US 2023/0201607 A1 Jun. 29, 2023

Related U.S. Application Data

(63) Continuation of application No. 17/025,573, filed on Sep. 18, 2020, now Pat. No. 11,666,766.

(60) Provisional application No. 62/903,155, filed on Sep. 20, 2019.

(51) Int. Cl.
*G16H 40/67* (2018.01)
*A61N 1/372* (2006.01)
(Continued)

(52) U.S. Cl.
CPC ..... *A61N 1/37254* (2017.08); *A61N 1/37282* (2013.01); *G06F 21/629* (2013.01); *G16H 40/63* (2018.01); *G16H 40/67* (2018.01)

(58) Field of Classification Search
CPC ............ A61N 1/37254; A61N 1/37282; G06F 21/44; G06F 21/629; G06F 2221/2129;
(Continued)

(56) References Cited

U.S. PATENT DOCUMENTS 7,155,290 B2 12/2006 Von Arx et al.
7,818,067 B2 10/2010 Healy et al.
(Continued)

FOREIGN PATENT DOCUMENTS

WO    WO 2019/239343 A1    12/2019

OTHER PUBLICATIONS

Mosenia, Arsalan, "OpSecure: A Secure Unidirectional Optical Channel for Implantable Medical Devices" IEEE Transactions on Multi-Scale Computing Systems, vol. 4, No. 3 Jul.-Sep. 2018.
(Continued)

*Primary Examiner* — George Manuel
(74) *Attorney, Agent, or Firm* — Michael P. Horvath

(57) ABSTRACT

In various examples, a method of establishing a communication session between an external device and an implantable medical device is described. The method includes generating at the external device a first private key and a first public key. A start session order is sent over a long-range communication channel. Evidence of physical proximity is sent from the external device to the implantable medical device over a short-range communication channel. A second private key and a second public key are generated at the implantable medical device. A first shared key is generated by the implantable medical device using the first public key and the second private key. A second shared key is generated by the external device using the second public key and the first private key. The first and second shared keys are used to encrypt and decrypt one or more messages between the external device and the implantable medical device.

20 Claims, 6 Drawing Sheets

(51) Int. Cl.
*G06F 21/62* (2013.01)
*G16H 40/63* (2018.01)

(58) Field of Classification Search
CPC .... G16H 40/63; G16H 40/67; H04L 2209/88; H04L 9/0841; H04L 9/0861; H04L 9/3215; H04L 9/3242; H04W 12/0431; H04W 12/63
See application file for complete search history.

(56) References Cited

U.S. PATENT DOCUMENTS

| | | |
|---|---|---|
| 7,831,828 B2 | 11/2010 | Von et al. |
| 8,265,770 B2 | 9/2012 | Toy et al. |
| 8,301,110 B2 | 10/2012 | Roberts et al. |
| 8,437,689 B2 | 5/2013 | Mazar |
| 8,868,201 B2 | 10/2014 | Roberts et al. |
| 8,995,949 B2 | 3/2015 | Roberts et al. |
| 9,318,916 B2 | 4/2016 | Olson et al. |
| 10,286,217 B2 | 5/2019 | Bornhoft et al. |
| 2017/0286614 A1 | 10/2017 | Morris et al. |
| 2018/0109946 A1 | 4/2018 | Mosenia et al. |
| 2018/0152454 A1* | 5/2018 | Kwon .................. H04L 63/045 |
| 2018/0309766 A1 | 10/2018 | Marnfeldt |
| 2019/0060654 A1 | 2/2019 | Ball et al. |

OTHER PUBLICATIONS

Rasmussen, Kasper B. et al., "Proximity-based Access Control for Implantable Medical Devices".

* cited by examiner

METHOD OF ESTABLISHING A COMMUNICATION SESSION BETWEEN AN EXTERNAL DEVICE AND AN IMPLANTABLE MEDICAL DEVICE

CROSS REFERENCE TO RELATED APPLICATIONS

This application is a continuation of and claims the benefit of priority under 35 U.S.C. § 120 to Nin et al., U.S. patent application Ser. No. 17/025,573, now U.S. Pat. No. 11,666,766, filed on Sep. 18, 2020, entitled "METHOD OF ESTABLISHING A COMMUNICATION SESSION BETWEEN AN EXTERNAL DEVICE AND AN IMPLANTABLE MEDICAL DEVICE," which claims the benefit of priority to U.S. Provisional Application Ser. No. 62/903,155, filed on Sep. 20, 2019, entitled "VOLATILE KEY ECDH AUTHENTICATION, BASED ON PHYSICAL PROXIMITY FOR IMDS," which is incorporated by reference herein in its entirety.

BACKGROUND

An attacker having unauthorized access to an implantable medical device can result in a dangerous and unwanted situation. An implantable medical device typically communicates with external equipment using a long-range communication channel, such as, for instance, a radio frequency (RF) communication channel. Without proper safeguards, such long-range communication channels can be vulnerable to attack allowing unauthorized access to the implantable medical device. Such unauthorized access could allow the attacker to send orders (which could carry dangerous settings) to an implantable medical device and/or decode an ongoing communication, which could pose a risk to the privacy and health of the patient within whom the implantable medical device is disposed.

OVERVIEW

This overview is intended to provide an overview of subject matter of the present patent document. It is not intended to provide an exclusive or exhaustive explanation of the invention. The detailed description is included to provide further information about the present patent document.

The present inventors have recognized, among other things, that the present subject matter can be used to authorize an external device using physical proximity, eliminating the need to use biometric data or secret/fixed cryptographic keys. In various examples, the present subject matter is advantageous in that it provides quick and simple authentication by providing evidence of physical proximity over an insecure, short-range communication channel. In some examples, the present invention enables the system to use volatile keys, which can change from session to session, adding to the security of the system. In some examples, the present invention can provide authorization only once, when the external device provides evidence of physical proximity, so the present invention can still take advantage of a long-range communication channel after that, while maintaining the security benefits of short-range communication channel authentication. To better illustrate the devices and methods described herein, a non-limiting list of examples is provided here:

Example 1 can include subject matter that can include a method of establishing a communication session between an external device and an implantable medical device. The method includes generating a first private key. The first private key is generated by the external device. A first public key is generated from the first private key. The first public key is generated by the external device. A start session order is sent from the external device to the implantable medical device over a long-range communication channel. Evidence of physical proximity is sent from the external device to the implantable medical device over a short-range communication channel. A second private key is generated. The second private key is generated by the implantable medical device. A second public key is generated from the second private key. The second public key is generated by the implantable medical device. The second public key is sent from the implantable medical device to the external device over the long-range communication channel. A first shared key is generated using the first public key and the second private key. The first shared key is generated by the implantable medical device and used by the implantable medical device to decrypt one or more messages from the external device during the communication session and/or encrypt one or more messages to the external device during the communication session. A second shared key is generated using the second public key and the first private key. The second shared key is generated by the external device and used by the external device to decrypt one or more messages from the implantable medical device during the communication session and/or encrypt one or more messages to the implantable medical device during the communication session.

In Example 2, the subject matter of Example 1 is optionally configured such that generating the first private key includes generating the first private key using a random number generator.

In Example 3, the subject matter of Example 1 or 2 is optionally configured such that generating the first private key using the random number generator includes generating the first private key using a cryptographically secure pseudorandom number generator.

In Example 4, the subject matter of any one of Examples 1-3 is optionally configured such that generating the first private key using the random number generator includes generating the first private key using a cryptographically secure random number generator.

In Example 5, the subject matter of any one of Examples 1-4 is optionally configured such that generating the first public key from the first private key includes calculating the first public key from the first private key.

In Example 6, the subject matter of Example 5 is optionally configured such that calculating the first public key from the first private key includes calculating the first public key from the first private key using an elliptic curve Diffie-Hellman algorithm.

In Example 7, the subject matter of any one of Examples 1-6 is optionally configured such that sending the start session order includes sending the start session order from the external device to the implantable medical device over a radio-frequency communication channel.

In Example 8, the subject matter of any one of Examples 1-7 is optionally configured such that sending the start session order includes sending an authentication code from the external device to the implantable medical device over the long-range communication channel.

In Example 9, the subject matter of Example 8 is optionally configured such that sending evidence of physical proximity includes sending the authentication code from the external device to the implantable medical device over the short-range communication channel.

In Example 10, the subject matter of Example 9 optionally includes comparing the authentication code received by the implantable medical device over the short-range communication channel to the authentication code received by the implantable medical device over the long-range communication channel and aborting the establishing of the communication session if the authentication code received by the implantable medical device over the short-range communication channel is not the same as the authentication code received by the implantable medical device over the long-range communication channel.

In Example 11, the subject matter of Example 9 or 10 optionally includes sending the first public key from the external device to the implantable device over the long-range communication channel.

In Example 12, the subject matter of any one of Examples 1-11 is optionally configured such that sending evidence of physical proximity includes sending the first public key from the external device to the implantable medical device over the short-range communication channel.

In Example 13, the subject matter of any one of Examples 1-12 is optionally configured such that generating the second private key includes generating the second private key using a random number generator.

In Example 14, the subject matter of any one of Examples 1-13 is optionally configured such that generating the second private key using the random number generator includes generating the second private key using a cryptographically secure pseudo-random number generator.

In Example 15, the subject matter of any one of Examples 1-14 is optionally configured such that generating the second private key using the random number generator includes generating the second private key using a cryptographically secure random number generator.

In Example 16, the subject matter of any one of Examples 1-15 is optionally configured such that generating the second public key from the second private key includes calculating the second public key from the second private key.

In Example 17, the subject matter of any one of Examples 1-16 is optionally configured such that calculating the second public key from the second private key includes calculating the second public key from the second private key using an elliptic curve Diffie-Hellman algorithm.

In Example 18, the subject matter of any one of Examples 1-17 is optionally configured such that sending the second public key includes sending the second public key from the implantable medical device to the external device over a radio-frequency communication channel.

In Example 19, the subject matter of any one of Examples 1-18 is optionally configured such that generating the first and second shared keys includes generating the first shared key that is the same as the second shared key. The first and second keys are used in a block cipher algorithm for encryption and/or decryption of the one or more messages between the external device and the implantable medical device.

In Example 20, the subject matter of any one of Examples 1-19 is optionally configured such that sending evidence of physical proximity from the external device to the implantable medical device over the short-range communication channel includes sending evidence of physical proximity between an external coil and a hall-effect sensor within the implantable medical device.

DETAILED DESCRIPTION

The present invention relates generally to establishing a secure communication session between an implantable medical device and an external device. More specifically, the present invention relates to establishing a secure communication session where the implantable medical device uses evidence of close physical proximity to the external device to authorize the communication. In some examples, such evidence is provided in a fast, secure, and simple way. In some examples, such evidence need only be provided once, so communication can resume later with a larger distance between the implantable medical device and the external device.

Figure 1:
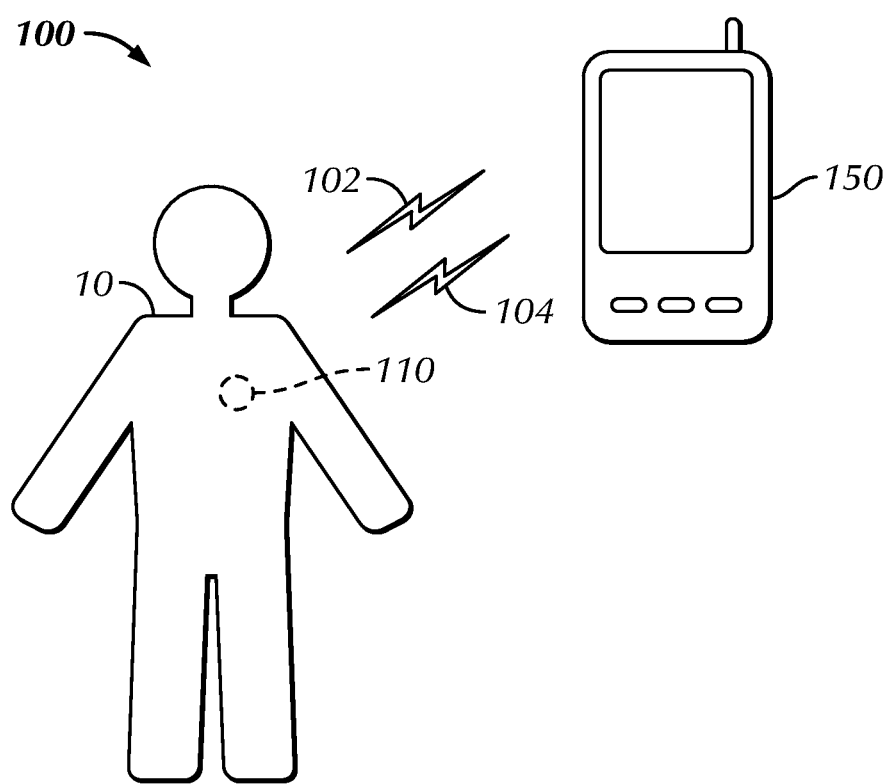
FIG. 1 depicts an implantable device and an external device configured to establish a communication session in accordance with at least one example of the invention.

Referring to FIG. 1, in some examples, a system 100 includes an implantable medical device 110. The implantable medical device 110, in various examples, can include various types of implantable medical devices, such as, but not limited to, a defibrillator, a pacemaker, a cardiac monitor, an insulin pump, or the like. In some examples, an external device 150 is used to program, set, or otherwise adjust the implantable medical device 110. The implantable medical device 110, in some examples, is implanted within a patient 10, and, once implanted, the implantable medical device 110 communicates wirelessly with the external device 150, for instance, to program, set, or otherwise adjust the implantable medical device 110 using the external device 150. In some examples, the implantable medical device 110 and the external device 110 can communicate with each other using a short-range communication channel 102, a long-range communication channel 104, or both the short-range communication channel 102 and the long-range communication channel 104.

In some examples, the short-range communication channel 102 can include a charge channel (an inductive coupling link) used to charge a battery on board the implantable medical device 110. In other examples, the short-range communication channel 102 can include a hall-effect sensor on board the implantable medical device 110 in conjunction with an external coil. Such short-range communication channels 102, in some examples, require close proximity of the external device to the implantable medical device 110 in order to allow communication between the external device 150 and the implantable medical device 110. In some examples, the external coil should be within a few centimeters of the implantable medical device 110 in order to allow communication through the short-range communication channel 102. In further examples, the external coil should can be within ten centimeters of the implantable medical device 110 in order to allow communication through the short-range communication channel 102. In still further examples, the external coil should be less than five centimeters from the implantable medical device 110 in order to allow communication through the short-range communication channel 102.

In some examples, the long-range communication channel 104 can include a radio-frequency (RF) communication channel. In other examples, other types of long-range communication channels 104 are contemplated. Such long-range communication channels 104 include a longer range than the short-range communication channel 102. In some examples, the long-range communication channel 104 includes a range of around twenty meters, depending upon the amount of obstructions, such as walls and/or tissue of the patient 10, for instance, between the implantable medical device 110 and the external device 150. In other examples, the long-range communication channel 104 can include a range of greater than twenty meters.

Figure 2:
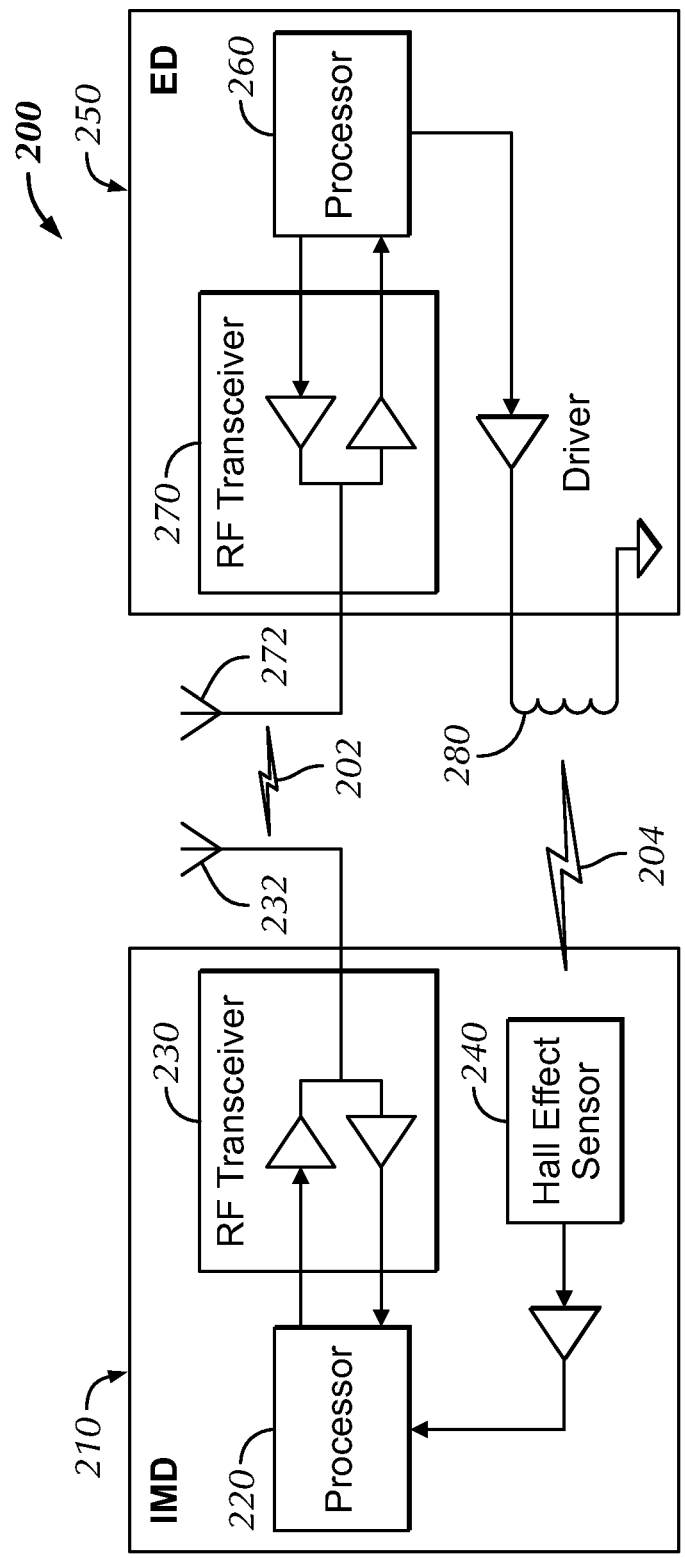
FIG. 2 is a diagram of an implantable device and an external device configured to establish a communication session in accordance with at least one example of the invention.

Referring to FIG. 2, a system 200 includes an implantable medical device 210 and an external device 250. In some examples, the implantable medical device 210 and the external device 250 are configured to communicate using a long-range communication channel 202 and a short-range communication channel 204.

In some examples, the implantable medical device 210 includes a processor 220 configured to perform various operations within the implantable medical device 210 to operate, control, and otherwise allow the implantable medical device 210 to function in its intended manner. In some examples, the processor 220 is operably connected to a RF transceiver 230 configured to allow communication with the external device 250 through the long-range communication channel 202. The RF transceiver 230, in some examples, is coupled to an antenna 232 of the implantable medical device 210 to receive and transmit RF waves. In some examples, the processor 220 is operably connected to a Hall effect sensor 240 configured to allow communication with the external device 250 through the short-range communication channel 204.

In some examples, the external device 250 includes a processor 260 configured to perform various operations within the external device 250 to operate, control, and otherwise allow the external device 250 to function in its intended manner. In some examples, the processor 260 is operably connected to a RF transceiver 270 configured to allow communication with the implantable medical device 210 through the long-range communication channel 202. The RF transceiver 270, in some examples, is coupled to an antenna 272 of the external device 250 to receive and transmit RF waves. In some examples, the processor 260 is operably connected to a coil 280 configured to allow communication with the implantable medical device 210 through the short-range communication channel 204. In some examples, the coil 280 can output a magnetic field which is capable of being sensed by the Hall effect sensor 240 of the implantable medical device 210 when the coil 280 and the Hall effect sensor 240 are within close proximity to one another. In some examples, in order for the Hall effect sensor 240 to sense the magnetic field of the coil 280, the coil 280 should be within a few centimeters of the Hall effect sensor 240. In further examples, in order for the Hall effect sensor 240 to sense the magnetic field of the coil 280, the coil 280 should be within ten centimeters of the Hall effect sensor 240. In still further examples, in order for the Hall effect sensor 240 to sense the magnetic field of the coil 280, the coil 280 should be less than five centimeters from the Hall effect sensor 240. Once within range of the coil 280, in some examples, the Hall effect sensor 240 can sense the magnetic field of the coil 280 to indicate to the implantable medical device 210 that the external device 250 is in close proximity to the implantable medical device 210, and, therefore, authenticate the external device 250 by proximity as described in more detail below.

Figure 3:
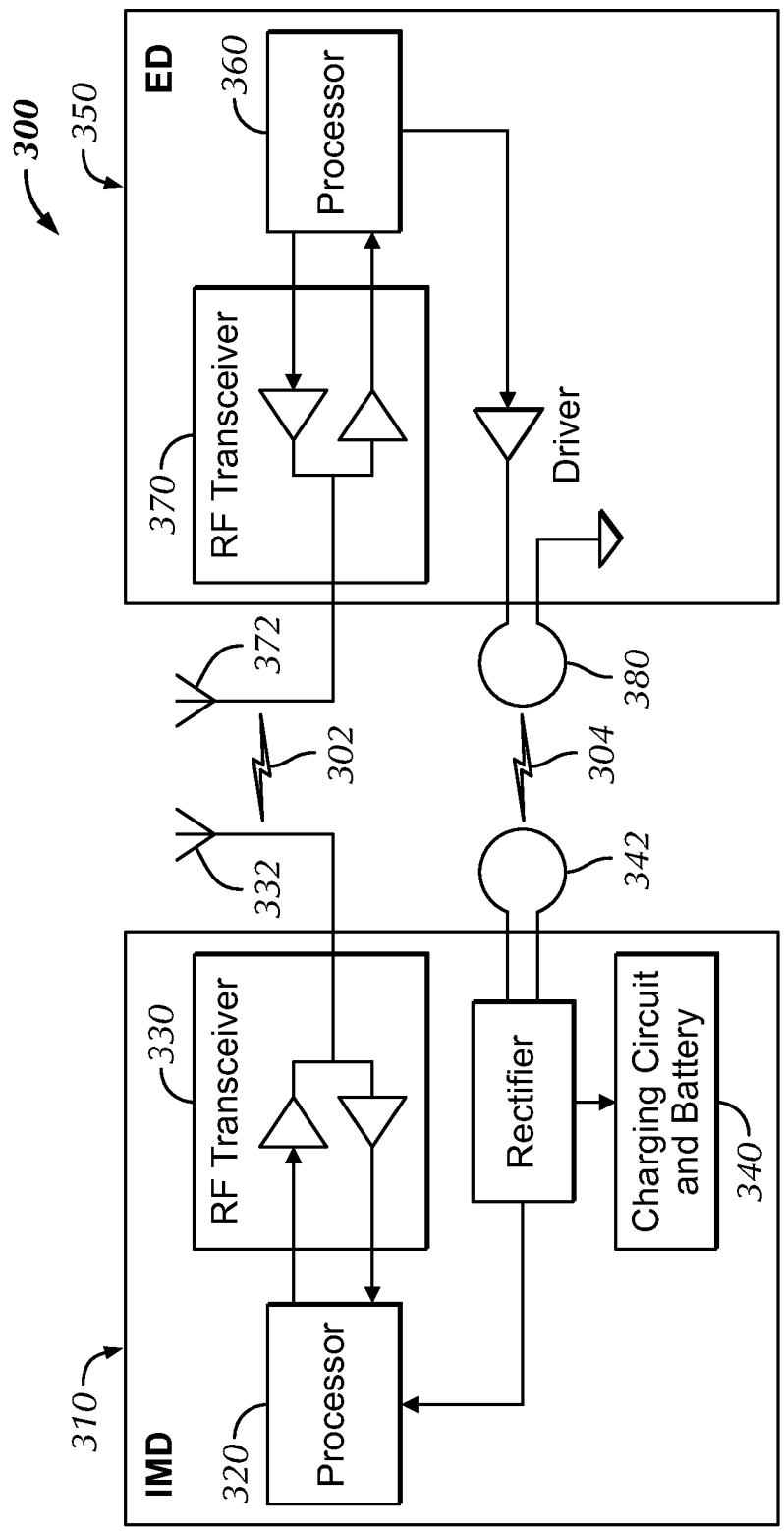
FIG. 3 is a diagram of an implantable device and an external device configured to establish a communication session in accordance with at least one example of the invention.

Referring to FIG. 3, a system 300 includes an implantable medical device 310 and an external device 350. In some examples, the implantable medical device 310 and the external device 350 are configured to communicate using a long-range communication channel 302 and a short-range communication channel 304.

In some examples, the implantable medical device 310 includes a processor 320 configured to perform various operations within the implantable medical device 310 to operate, control, and otherwise allow the implantable medical device 310 to function in its intended manner. In some examples, the processor 320 is operably connected to a RF transceiver 330 configured to allow communication with the external device 350 through the long-range communication channel 302. The RF transceiver 330, in some examples, is coupled to an antenna 232 of the implantable medical device 310 to receive and transmit RF waves. In some examples, the processor 320 is operably connected to a charging circuit 340 configured to charge a battery within the implantable medical device 310. The charging circuit 340, in some examples, is operably coupled to a charge coil 342 of the implantable medical device 310 couplable to the external device 350 to charge the battery. Additionally, in some examples, the charging circuit 340 and the charge coil 342 can also be configured to allow communication with the external device 350 through the short-range communication channel 304.

In some examples, the external device 350 includes a processor 360 configured to perform various operations within the external device 350 to operate, control, and otherwise allow the external device 350 to function in its intended manner. In some examples, the processor 360 is operably connected to a RF transceiver 370 configured to allow communication with the implantable medical device 310 through the long-range communication channel 302. The RF transceiver 370, in some examples, is coupled to an antenna 372 of the external device 350 to receive and transmit RF waves. In some examples, the processor 360 is operably connected to a coil 380 configured to inductively couple to the charge coil 342 of the implantable medical device 310 in order to allow charging of the battery of the implantable medical device 310 by the external device 350. In some examples, the coil 380 of the external device 350 can also allow communication with the implantable medical device 310 through the short-range communication channel 304. In some examples, the coil 380 can inductively couple with the charge coil 342 of the implantable medical device 310 when the coil 380 and the charge coil 342 are within close proximity to one another. In some examples, in order for the charge coil 342 to inductively couple to the coil 380, the coil 380 should be within a few centimeters of the charge coil 342. In further examples, in order for the charge coil 342 to inductively couple to the coil 380, the coil 380 should be within ten centimeters of the charge coil 342. In still further examples, in order for the charge coil 342 to inductively couple to the coil 380, the coil 380 should be less than five centimeters from the charge coil 342. In this way, in some examples, the inductive coupling of the coil 380 of the external device 350 and the charge coil 342 of the implantable medical device 310 allows for power transfer from the external device 350 to the implantable medical device 310 in order to charge the battery. Also, in some examples, once the charge coil 342 is within range of the coil 380, the inductive coupling of the charge coil 342 and the coil 380 can create the short-range communication channel 304 in order to indicate to the implantable medical device 310 that the external device 350 is in close proximity to the implantable medical device 310, and, therefore, authenticate the external device 350 by proximity as described in more detail below. In some examples, short-range communication is accomplished by modulating the charge signal, thereby using the same hardware that is used to charge the battery of the implantable medical device 310 and, thus, having a minimum impact on the required hardware within the implantable medical device 310.

Referring now to FIGS. 1-3, in some examples, physical proximity is used to authorize the external device 150, 250, 350, so no biometric data or secret/fixed cryptographic keys are used. Together with the speed and simplicity of the method, as described in more detail below, this enables the system 100, 200, 300, in some examples, to use volatile keys (that is, the keys can change from session to session), which increase the security of the system 100, 200, 300. In some examples, the method works even if the evidence of physical proximity is provided over an insecure short-range communication channel 104, 204, 304. Use of physical proximity of the external device 150, 250, 350 to grant authorization through the short-range communication channel 104, 204, 304 during the generation of the encryption key, in some examples, implies that any device in possession of a key was, at some point, in physical proximity of the implantable medical device 110, 210, 310.

In some examples, the authorization need only occur once (such as, for instance, when the external device 150, 250, 350 provides evidence of physical proximity), so that the system 100, 200, 300 can still take advantage of the long-range communication channel 102, 202, 302 after that, while maintaining the security benefits of short-range communication channel 104, 204, 304.

Evidence of physical proximity of the external device 150, 250, 350 is provided through the short-range communication channel 104, 204, 304, but, in some examples, the short-range communication channel 104, 204, 304 can be unidirectional. That is, in some examples, the implantable medical device 110, 210, 310 only needs to receive or transmit over the short-range communication channel 104, 204, 304, not both. This simplifies the hardware on the implantable medical device 110, 210, 310, thereby reducing cost, size, and complexity of the implantable medical device 110, 210, 310. In other examples, however, the short-range communication channel 104, 204, 304 can be bi-directional, such that the implantable medical device 110, 210, 310 is configured to receive and transmit over the short-range communication channel 104, 204, 304.

Figure 4:
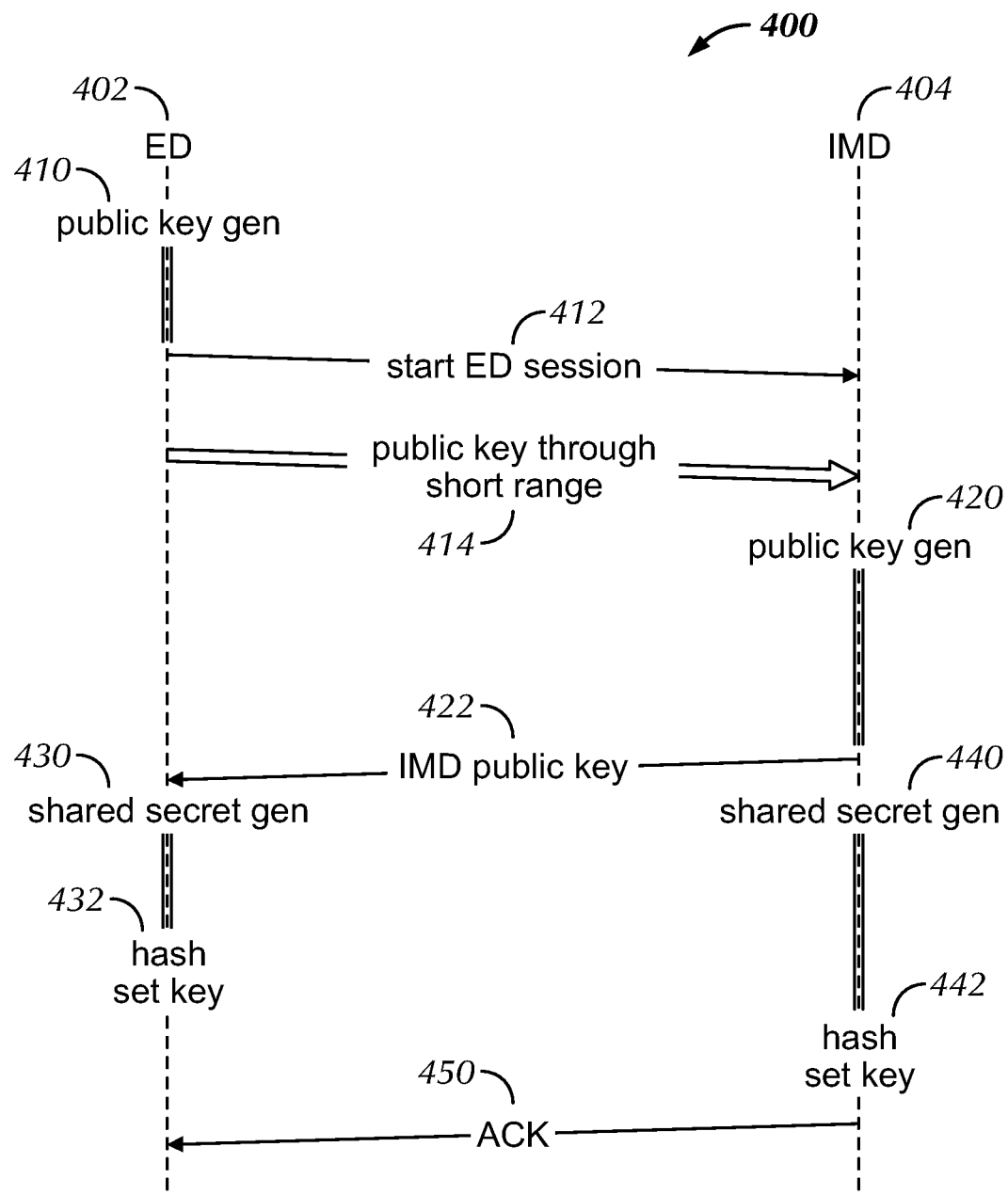
FIG. 4 is a diagram of a method of establishing a communication session between an implantable device and an external device in accordance with at least one example of the invention.

Referring to FIG. 4, an example of a method 400 of establishing a communication session between an external device 402 and an implantable medical device 404 is shown. In some examples, the external device 402 can be similar to or otherwise include one or more features of one or more of the external devices 150, 250, 350 described above, and/or the implantable medical device 404 can be similar to or otherwise include one or more features of one or more of the implantable medical devices 110, 210, 310 described above.

In some examples, a first private key is generated by the external device 402. The first private key can be generated in various ways. In some examples, the first private key is generated using a random number generator. In some examples, the random number generator is a device, mechanism, or component configured to produce a number as a function of a current value of a physical variable that cannot be easily modeled or predicted. In further examples, the first private key is generated using a cryptographically secure pseudo-random number generator. In some examples, a pseudo-random number generator is a device, mechanism, or component configured to produce numbers that appear random, but are actually deterministic and can be predicted knowing the state of the pseudo-random number generator and the law it follows to generate them. A cryptographically secure pseudo-random number generator, in further examples, is a pseudo-random number generator device, mechanism, or component that has certain properties that make it suitable for cryptographic applications, such as higher entropy and tougher randomness tests. In other examples, the first private key is generated using a cryptographically secure random number generator. A cryptographically secure random number generator, in some examples, is a random number generator device, mechanism, or component that has certain properties that make it suitable for cryptographic applications, such as higher entropy and tougher randomness tests. Once the first private key is generated, the external device 402 generates, at 410, a first public key from the first private key. In some examples, generating the first public key from the first private key includes calculating the first public key from the first private key. In further examples, the first public key is calculated from the first private key using an elliptic curve Diffie-Hellman (ECDH) algorithm.

In some examples, at 412, a start session order is sent from the external device 402 to the implantable medical device 404 over a long-range communication channel. In some examples, the long-range communication channel can be similar to or otherwise include one or more features of one or more of the long-range communication channels 102, 202, 302 described above. In some examples, the start session order is sent from the external device 402 to the implantable medical device 404 over a RF communication channel.

In some examples, at 414, evidence of physical proximity is sent from the external device 402 to the implantable medical device 404 over a short-range communication channel. In some examples, the short-range communication channel can be similar to or otherwise include one or more features of one or more of the short-range communication channels 104, 204, 304 described above. In some examples, sending evidence of physical proximity 414 includes sending the first public key from the external device 402 to the implantable medical device 404 over the short-range communication channel. In some examples, evidence of physical proximity is sent from the external device 402 to the implantable medical device 404 over the short-range communication channel, which is similar to the short-range communication channel 204 described above between the Hall effect sensor 240 within the implantable medical device 210 and the external coil 280 of the external device 250. In some examples, evidence of physical proximity is sent from the external device 402 to the implantable medical device 404 over the channel used to charge the implantable medical device 404, which is similar to the short-range communication channel 304 described above between the charge coil 342 of the implantable medical device 310 and the coil 380 of the external device 350.

In some examples, a second private key is generated by the implantable medical device 404. The second private key can be generated in various ways. In some examples, the second private key is generated using a random number generator. In further examples, the second private key is generated using a cryptographically secure pseudo-random number generator. In other examples, the second private key is generated using a cryptographically secure random number generator. Once the second private key is generated, the implantable medical device 404 generates, at 420, a second public key from the second private key. In some examples, generating the second public key from the second private key includes calculating the second public key from the second private key. In further examples, the second public key is calculated from the second private key using an elliptic curve Diffie-Hellman (ECDH) algorithm.

At 422, in some examples, the second public key is sent from the implantable medical device 404 to the external device 402 over the long-range communication channel. In some examples, the second public key is sent from the implantable medical 404 device to the external device 402 over a RF communication channel.

Once the second public key generated by the implantable medical device 404 is shared with the external device 402 and the first public key generated by the external device 402 is shared with the implantable medical device 404, in some examples, shared keys are generated by each of the external device 402 and the implantable medical device 404. In further examples, a first shared key is generated, at 440, by the implantable medical device 404 using the first public key (received by the implantable medical device 404 from the external device 402) and the second private key that the implantable medical device 404 generated. In some examples, the first shared key is used by the implantable medical device 404 to decrypt one or more messages from the external device 402 during the communication session and/or encrypt one or more messages to the external device 402 during the communication session. In still further examples, a second shared key is generated, at 430, by the external device 402 using the second public key (received by the external device 402 from the implantable medical device 404) and the first private key that the external device 402 generated. In some examples, the second shared key is used by the external device 402 to decrypt one or more messages from the implantable medical device 404 during the communication session and/or encrypt one or more messages to the implantable medical device 404 during the communication session.

In some examples, when the method 400 of establishing the communication session is performed correctly, the first shared key generated by the implantable medical device 404 is the same as the second shared key generated by the external device 402. In this way, in some examples, the first and second keys can be used in a block cipher algorithm for encryption and decryption of the one or more messages between the external device 402 and the implantable medical device 404. In some examples, the external device 402 can hash, at 432, the second shared key, using a hash function and then use the hashed second shared key to encrypt and/or decrypt messages during the communication session. In some examples, the implantable medical device 404 can hash, at 442, the first shared key, using a hash function and then use the hashed first shared key to encrypt and/or decrypt messages during the communication session.

In some examples, a hash function maps data of arbitrary size to a fixed-size value, in a non-invertible and uniform fashion. That said, in other examples, one or both of the implantable medical device 404 and the external device 402 can just use the unhashed first and second shared keys, respectively, to encrypt and/or decrypt messages during the communication session.

Once the first and second shared keys are generated, an acknowledgement of the start of the communication session is sent, at 450, from the implantable medical device 404 to the external device 402, and the communication session is established.

Figure 5:
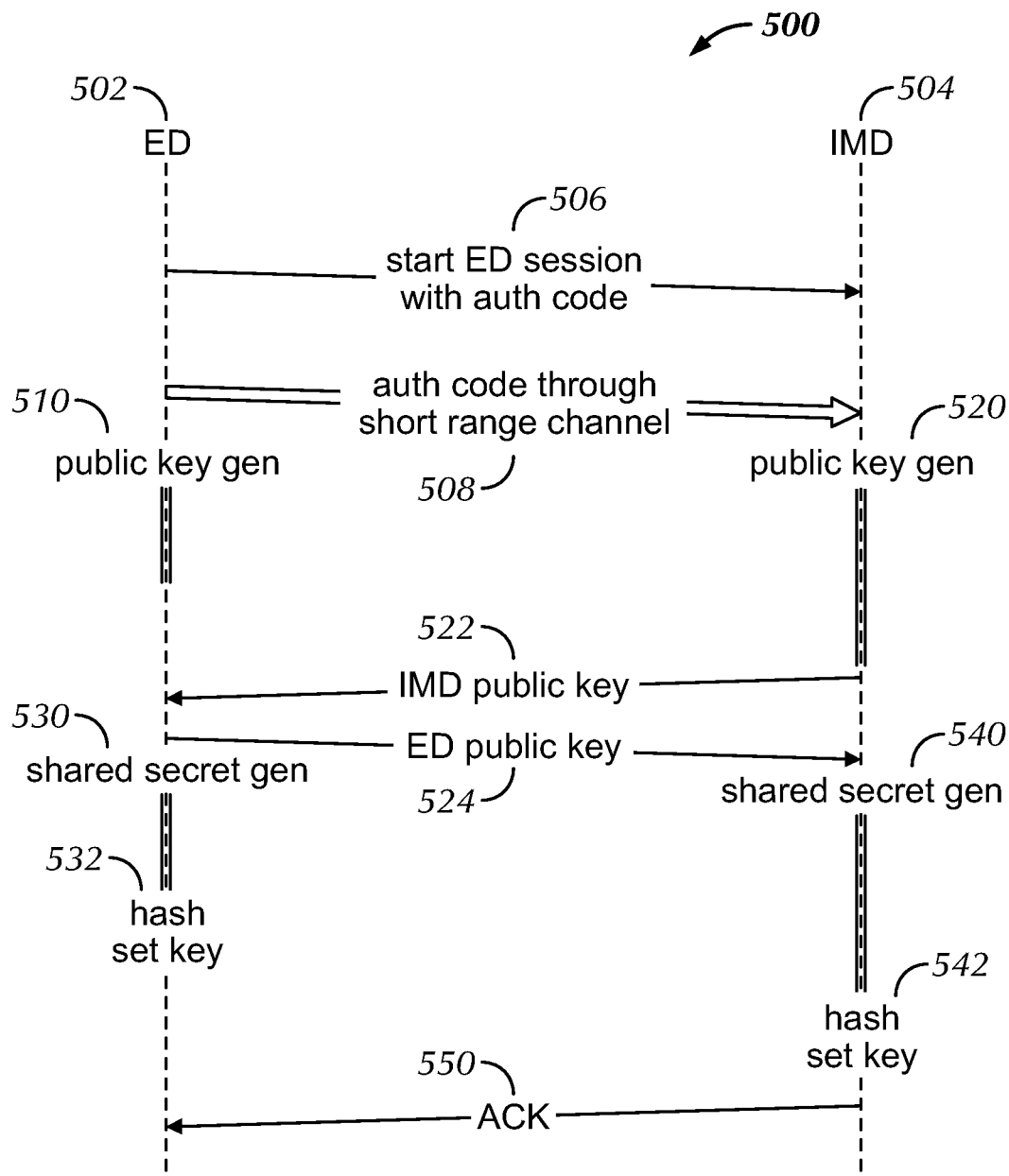
FIG. 5 is a diagram of a method of establishing a communication session between an implantable device and an external device in accordance with at least one example of the invention.

Referring to FIG. 5, an example of a method 500 of establishing a communication session between an external device 502 and an implantable medical device 504 is shown. In some examples, the external device 502 can be similar to or otherwise include one or more features of one or more of the external devices 150, 250, 350 described above, and/or the implantable medical device 504 can be similar to or otherwise include one or more features of one or more of the implantable medical devices 110, 210, 310 described above.

In some examples, at 506, a start session order is sent from the external device 502 to the implantable medical device 504 over a long-range communication channel. In some examples, the long-range communication channel can be similar to or otherwise include one or more features of one or more of the long-range communication channels 102, 202, 302 described above. In some examples, the start session order is sent from the external device 502 to the implantable medical device 504 over a RF communication channel. In some examples, along with sending 506 the start session order, the external device 502, generates and sends an authentication code from the external device 502 to the implantable medical device 504 over the long-range communication channel. In various examples, the authentication code can be generated in various ways. In some examples, the authentication code is generated using a random number generator. In further examples, the authentication code is generated using a cryptographically secure pseudo-random number generator. In other examples, the authentication code is generated using a cryptographically secure random number generator.

In some examples, at 508, evidence of physical proximity is sent from the external device 502 to the implantable medical device 504 over a short-range communication channel. In some examples, the short-range communication channel can be similar to or otherwise include one or more features of one or more of the short-range communication channels 104, 204, 304 described above. In some examples, sending evidence of physical proximity 514 includes sending the authentication code from the external device 502 to the implantable medical device 504 over the short-range communication channel. In some examples, evidence of physical proximity is sent from the external device 502 to the implantable medical device 504 over the short-range communication channel, which is similar to the short-range communication channel 204 described above between the Hall effect sensor 240 within the implantable medical device 210 and the external coil 280 of the external device 250. In some examples, evidence of physical proximity is sent from the external device 502 to the implantable medical device 504 over the channel used to charge the implantable medical device 504, which is similar to the short-range communication channel 304 described above between the charge coil 342 of the implantable medical device 310 and the coil 380 of the external device 350.

In some examples, the authentication code received by the implantable medical device 504 over the short-range communication channel is compared to the authentication code received by the implantable medical device 504 over the long-range communication channel. In some examples, if the authentication code received by the implantable medical device 504 over the short-range communication channel is the same as the authentication code received by the implantable medical device 504 over the long-range communication channel, the method 500 of establishing the communication session is allowed to proceed. In some examples, if the authentication code received by the implantable medical device 504 over the short-range communication channel is not the same as the authentication code received by the implantable medical device 504 over the long-range communication channel, the method 500 of establishing the communication session is aborted.

If the method 500 of establishing the communication session is allowed to proceed, in some examples, a first private key is generated by the external device 502. The first private key can be generated in various ways. In some examples, the first private key is generated using a random number generator. In further examples, the first private key is generated using a cryptographically secure pseudo-random number generator. In other examples, the first private key is generated using a cryptographically secure random number generator. Once the first private key is generated, the external device 502 generates, at 510, a first public key from the first private key. In some examples, generating the first public key from the first private key includes calculating the first public key from the first private key. In further examples, the first public key is calculated from the first private key using an elliptic curve Diffie-Hellman (ECDH) algorithm.

In some examples, a second private key is generated by the implantable medical device 504. The second private key can be generated in various ways. In some examples, the second private key is generated using a random number generator. In further examples, the second private key is generated using a cryptographically secure pseudo-random number generator. In other examples, the second private key is generated using a cryptographically secure random number generator. Once the second private key is generated, the implantable medical device 504 generates, at 520, a second public key from the second private key. In some examples, generating the second public key from the second private key includes calculating the second public key from the second private key. In further examples, the second public key is calculated from the second private key using an elliptic curve Diffie-Hellman (ECDH) algorithm.

At 522, in some examples, the second public key is sent from the implantable medical device 504 to the external device 502 over the long-range communication channel. In some examples, the second public key is sent from the implantable medical 504 device to the external device 502 over a RF communication channel. At 524, in some examples, the first public key is sent from the external device 502 to the implantable device 504 over the long-range communication channel.

Once the second public key generated by the implantable medical device 504 is shared with the external device 502 and the first public key generated by the external device 502 is shared with the implantable medical device 504, in some examples, shared keys are generated by each of the external device 502 and the implantable medical device 504. In further examples, a first shared key is generated, at 540, by the implantable medical device 504 using the first public key (received by the implantable medical device 504 from the external device 502) and the second private key that the implantable medical device 504 generated. In some examples, the first shared key is used by the implantable medical device 504 to decrypt one or more messages from the external device 502 during the communication session and/or encrypt one or more messages to the external device 502 during the communication session. In still further examples, a second shared key is generated, at 530, by the external device 502 using the second public key (received by the external device 502 from the implantable medical device 504) and the first private key that the external device 502 generated. In some examples, the second shared key is used by the external device 502 to decrypt one or more messages from the implantable medical device 504 during the communication session and/or encrypt one or more messages to the implantable medical device 504 during the communication session.

In some examples, when the method 500 of establishing the communication session is performed correctly, the first shared key generated by the implantable medical device 504 is the same as the second shared key generated by the external device 502. In this way, in some examples, the first and second keys can be used in a block cipher algorithm for encryption and decryption of the one or more messages between the external device 502 and the implantable medical device 504. In some examples, the external device 502 can hash, at 532, the second shared key, using a hash function and then use the hashed second shared key to encrypt and/or decrypt messages during the communication session. In some examples, the implantable medical device 504 can hash, at 542, the first shared key, using a hash function and then use the hashed first shared key to encrypt and/or decrypt messages during the communication session. That said, in other examples, one or both of the implantable medical device 504 and the external device 502 can just use the unhashed first and second shared keys, respectively, to encrypt and/or decrypt messages during the communication session.

Once the first and second shared keys are generated, an acknowledgement of the start of the communication session is sent, at 550, from the implantable medical device 504 to the external device 502, and the communication session is established.

Figure 6:
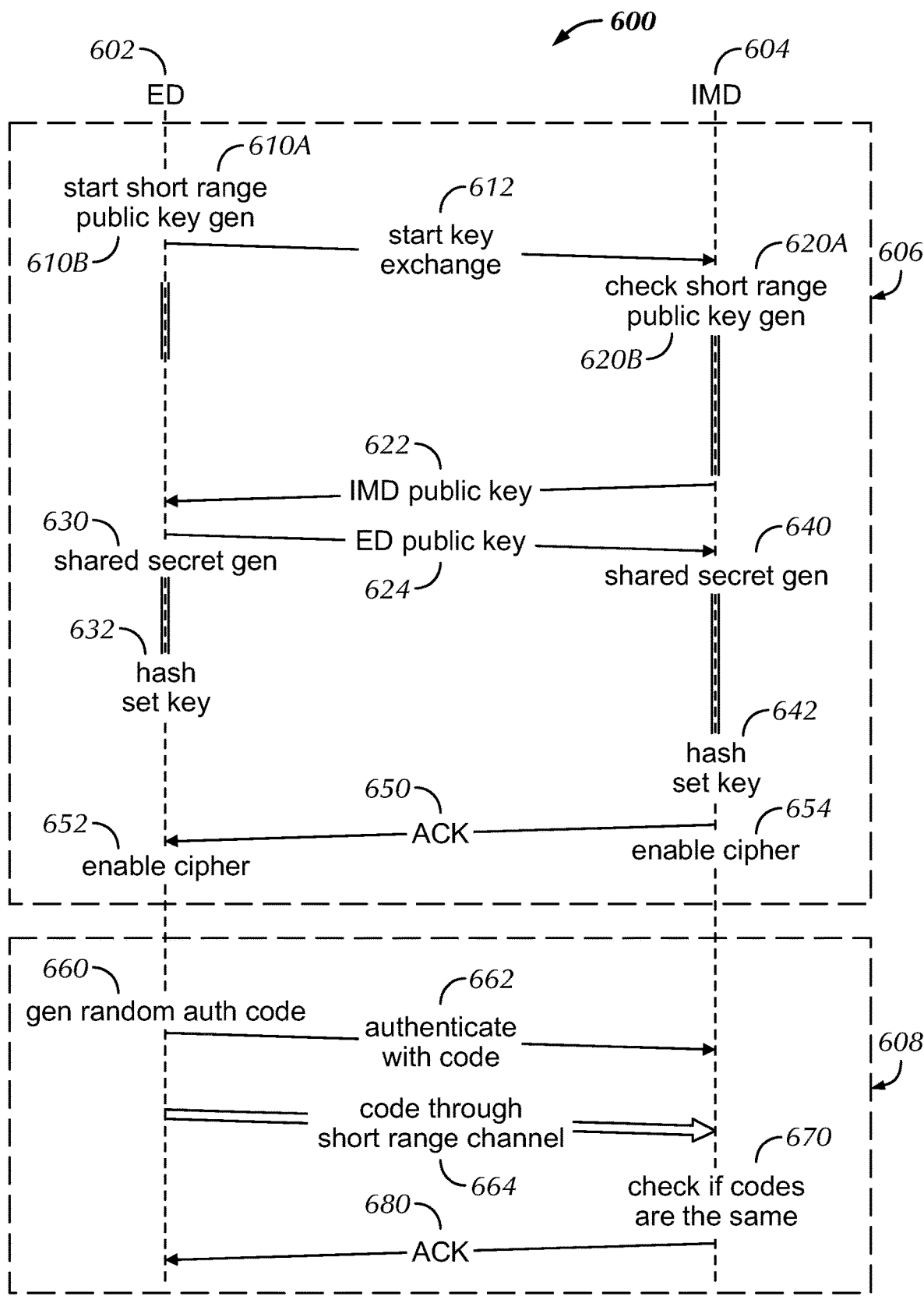
FIG. 6 is a diagram of a method of establishing a communication session between an implantable device and an external device in accordance with at least one example of the invention.

Referring to FIG. 6, an example of a method 600 of establishing a communication session between an external device 602 and an implantable medical device 604 is shown. In some examples, the external device 602 can be similar to or otherwise include one or more features of one or more of the external devices 150, 250, 350 described above, and/or the implantable medical device 604 can be similar to or otherwise include one or more features of one or more of the implantable medical devices 110, 210, 310 described above.

In some examples, the method 600 of establishing the communication session is substantially similar to the method 500 of establishing the communication session described above except that the method 600 separates key generation 606 from authentication 608. In some examples, separating the key generation 606 from the authentication 608 allows for encrypted and unauthenticated connections. In some examples, unauthenticated communication sessions do not have the same privileges as authenticated communication sessions. That said, in some examples, unauthenticated communication sessions can allow for some basic information exchange without authentication, such as, but not limited to IMD global status, battery state, charging information, and the like. In this way, in various examples, authentication 608 becomes optional.

In some examples, the method 600 begins with the external device 602 starting short range 610A and the implantable medical device 604 checking short range 620A, which provides some level of authentication, albeit not as secure as authenticating with an authorization code, as described above in the method 500 and below in the authentication 608 of the method 600. This exists, in some examples, because generation of the second public key in the implantable medical device 604 can consume a considerable amount of charge of a battery of the implantable medical device 604. Without some level of authentication, in some examples, an attacker could just send a "start key exchange" order to the implantable medical device 604 over and over, until the battery of the implantable medical device 604 is depleted. To minimize this risk, in some examples, the method 600 requires that the implantable medical device 604 checks the short range 620A first. In some examples, the external device 602 starts the short range 610A by turning on a short-range communication channel. In some examples, the short-range communication channel can be similar to or otherwise include one or more features of one or more of the short-range communication channels 104, 204, 304 described above. The external device 602, in various examples, can send various messages or signals through the short-range communication channel so that the implantable medical device 604 can discern that the short-range communication channel is on. In some examples, the external device 602 does not send any particular message but, rather, sends a signal that can be measured as being "ON" or "OFF" and sends a message to the implantable medical device 604 to start the key exchange. In some examples, the implantable medical device 604 receives the message and, before generating a second public key (which can be expensive from the battery consumption perspective), the implantable medical device 604 checks the short range 620A to make sure the external device 602 is not an attacker. In some examples, the implantable medical device 604 must determine that the short-range communication channel is "ON" before proceeding. In other examples, the implantable medical device 604 can protect itself against this kind of attack by not allowing consecutive "start short range" orders until a certain time has elapsed, thereby effectively limiting how fast the attacker can deplete the battery. In still other examples, the implantable medical device 604 need not check short range 620A prior to generating the second public key, for instance, if attackers depleting the battery of the implantable medical device 604 is not a concern.

In some examples, a first private key is generated by the external device 602. The first private key can be generated in various ways. In some examples, the first private key is generated using a random number generator. In further examples, the first private key is generated using a cryptographically secure pseudo-random number generator. In other examples, the first private key is generated using a cryptographically secure random number generator. Once the first private key is generated, the external device 602 generates, at 610B, a first public key from the first private key, regardless of whether the short range is started 610A and checked 620A. In some examples, generating the first public key from the first private key includes calculating the first public key from the first private key. In further examples, the first public key is calculated from the first private key using an elliptic curve Diffie-Hellman (ECDH) algorithm.

In some examples, a second private key is generated by the implantable medical device 604. The second private key can be generated in various ways. In some examples, the second private key is generated using a random number generator. In further examples, the second private key is generated using a cryptographically secure pseudo-random number generator. In other examples, the second private key is generated using a cryptographically secure random number generator. Once the second private key is generated, the implantable medical device 604 generates, at 620B, a second public key from the second private key. As described above, in some examples, the generation 620B of the second public key can proceed after checking the short range 620A. In other examples, the generation 620B of the second public key can proceed without checking the short range 620A. In some examples, generating the second public key from the second private key includes calculating the second public key from the second private key. In further examples, the second public key is calculated from the second private key using an elliptic curve Diffie-Hellman (ECDH) algorithm.

At 622, in some examples, the second public key is sent from the implantable medical device 604 to the external device 602 over a long-range communication channel. In some examples, the long-range communication channel can be similar to or otherwise include one or more features of one or more of the long-range communication channels 102, 202, 302 described above. In some examples, the second public key is sent from the implantable medical 604 device to the external device 602 over a RF communication channel. At 624, in some examples, the first public key is sent from the external device 602 to the implantable medical device 604 over the long-range communication channel.

Once the second public key generated by the implantable medical device 604 is shared with the external device 602 and the first public key generated by the external device 602 is shared with the implantable medical device 604, in some examples, shared keys are generated by each of the external device 602 and the implantable medical device 604. In further examples, a first shared key is generated, at 640, by the implantable medical device 604 using the first public key (received by the implantable medical device 604 from the external device 602) and the second private key that the implantable medical device 604 generated. In some examples, the first shared key is used by the implantable medical device 604 to decrypt one or more messages from the external device 602 during the communication session and/or encrypt one or more messages to the external device 602 during the communication session. In still further examples, a second shared key is generated, at 630, by the external device 602 using the second public key (received by the external device 602 from the implantable medical device 604) and the first private key that the external device 602 generated. In some examples, the second shared key is used by the external device 602 to decrypt one or more messages from the implantable medical device 604 during the communication session and/or encrypt one or more messages to the implantable medical device 604 during the communication session.

In some examples, when the method 600 of establishing the communication session is performed correctly, the first shared key generated by the implantable medical device 604 is the same as the second shared key generated by the external device 602. In this way, in some examples, the first and second keys can be used in a block cipher algorithm for encryption and decryption of the one or more messages between the external device 602 and the implantable medical device 604. In some examples, the external device 602 can hash, at 632, the second shared key, using a hash function and then use the hashed second shared key to encrypt and/or decrypt messages during the communication session. In some examples, the implantable medical device 604 can hash, at 642, the first shared key, using a hash function and then use the hashed first shared key to encrypt and/or decrypt messages during the communication session. That said, in other examples, one or both of the implantable medical device 604 and the external device 602 can just use the unhashed first and second shared keys, respectively, to encrypt and/or decrypt messages during the communication session.

Once the first and second shared keys are generated, an acknowledgement of the start of the communication session is sent, at 650, from the implantable medical device 604 to the external device 602, and an unauthenticated communication session is established. With the sending of the acknowledgment 650, the external device 602 can enable the cipher at 652, and the implantable medical can enable the cipher at 654 in order to allow for an information exchange between the implantable medical device 604 and the external device 602 in an unauthenticated communication session. The unauthenticated communication session can be used, in some examples, for some basic information exchange, such as exchanging information including, but not limited to, IMD global status, battery state, charging information, and the like.

In some examples, if a secure authenticated communication session is required or otherwise desired, the method 600 can proceed to authentication 608. In some examples, the external device 602, generates 660 and sends 662 an authentication code from the external device 602 to the implantable medical device 604 over the long-range communication channel. In various examples, the authentication code can be generated in various ways. In some examples, the authentication code is generated using a random number generator. In further examples, the authentication code is generated using a cryptographically secure pseudo-random number generator. In other examples, the authentication code is generated using a cryptographically secure random number generator.

In some examples, at 664, evidence of physical proximity is sent from the external device 602 to the implantable medical device 604 over a short-range communication channel. In some examples, sending evidence of physical proximity 664 includes sending the authentication code from the external device 602 to the implantable medical device 604 over the short-range communication channel. In some examples, evidence of physical proximity is sent from the external device 602 to the implantable medical device 604 over the short-range communication channel, which is similar to the short-range communication channel 204 described above between the Hall effect sensor 240 within the implantable medical device 210 and the external coil 280 of the external device 250. In some examples, evidence of physical proximity is sent from the external device 602 to the implantable medical device 604 over the channel used to charge the implantable medical device 604, which is similar to the short-range communication channel 304 described above between the charge coil 342 of the implantable medical device 310 and the coil 380 of the external device 350.

In some examples, the authentication code received by the implantable medical device 504 over the short-range communication channel is compared 670 to the authentication code received by the implantable medical device 604 over the long-range communication channel. In some examples, if the authentication code received by the implantable medical device 604 over the short-range communication channel is the same as the authentication code received by the implantable medical device 604 over the long-range communication channel, the method 600 of establishing the communication session is allowed to proceed. In some examples, if the authentication code received by the implantable medical device 604 over the short-range communication channel is not the same as the authentication code received by the implantable medical device 604 over the long-range communication channel, the method 600 of establishing the communication session is aborted.

If the authentication code received by the implantable medical device 604 over the short-range communication channel is determined to be the same as the authentication code received by the implantable medical device 604 over the long-range communication channel, in some examples, an acknowledgement of the start of the communication session is sent, at 680, from the implantable medical device 604 to the external device 602, and the authenticated communication session is established, allowing for the secured exchange of information between the external device 602 and the implantable medical device 604.

In various examples, the systems 100, 200, 300 and the methods 400, 500, 600 described herein use a short-range communication channel 104, 204, 304 to guarantee proximity and authenticate, as well as a key generation algorithm to create a symmetric first and second shared keys over an insecure, long-range communication channel 102, 202, 302 (for instance, a RF channel). After the key generation, messages are ciphered (for instance, with an advanced encryption standard (AES) block cipher) and authenticated with a fixed signature. In some examples, the implantable medical device 110, 210, 310, 404, 504, 604 only accepts one non-authenticated message, which is the start session order. In some examples, the external device 150, 250, 350, 402, 502, 602 that connects for the first time to the implantable medical device 110, 210, 310, 404, 504, 604 must establish a symmetric shared key and authenticate with the external device 150, 250, 350, 402, 502, 602. After that, in some examples, the external device 150, 250, 350, 402, 502, 602 can send encrypted orders with the symmetric shared key. In some examples, the implantable medical device 110, 210, 310, 404, 504, 604 will try to decrypt and carry out the order if it is valid.

After the communication session is started, the first and second shared keys generated by the implantable medical device 110, 210, 310, 404, 504, 604 and the external device 150, 250, 350, 402, 502, 602, respectively, are stored in the implantable medical device 110, 210, 310, 404, 504, 604 and the external device 150, 250, 350, 402, 502, 602. In this way, in some examples, the communication session can stop and be resumed later without the need to reauthenticate. Possession of the shared key implies authenticity, so, in some examples, when the external device 150, 250, 350, 402, 502, 602 wishes to communicate with the implantable medical device 110, 210, 310, 404, 504, 604, the external device 150, 250, 350, 402, 502, 602 sends a message encrypted with the shared key that was generated during the starting of the communication session. The message itself should have some sort of integrity check, so, in some examples, the implantable medical device 110, 210, 310, 404, 504, 604 can decrypt the message and tell whether the message came from a device with the correct key and execute the order.

In various examples, public key generation can be performed by various public key cryptography solutions. In further examples, public key generation can be performed by a Diffie-Hellman algorithm ported to an embedded system, including, but not limited to FourQ, libtomcrypt, microECC, nanoECC, and Curve25519.

In various examples, the systems 100, 200, 300 and the methods 400, 500, 600 described herein are advantageous in that they do not implement an explicit "telemetry interlock" and thus, no command is needed to release it. In some examples, the implantable medical device 110, 210, 310, 404, 504, 604 attempts to decrypt each message and, since the session keys are generated only when evidence of physical proximity is present, a successfully decrypted order is executed. This is more flexible than telemetry interlock, as it allows the authentication to persist in time for a desired amount of time. In this way, in various examples, the communication session can be interrupted and resumed later an arbitrary number of times, without the need of physical proximity to release a telemetry interlock each time.

In various examples, the systems 100, 200, 300 and the methods 400, 500, 600 described herein are advantageous in that they use volatile keys generated with evidence of physical proximity rather than fixed keys that are stored in the device memory by the manufacturer. Although fixed keys are simpler to implement, they pose several security risks because fixed keys can become more easily compromised, either by the design or a device being stolen, or because the key has been guessed. In such cases, a device can be recalled because the device is at risk of being accessed by an unauthorized user that happens to be in telemetry range of the device with a released telemetry interlock, which costs a company money for both the recall and the fix of the device. Furthermore, every recorded telemetry session might be decrypted with the fixed key, thereby compromising a patient's privacy. The volatile keys generated by the systems 100, 200, 300 and the methods 400, 500, 600 of the present subject matter are evidence of an authorized user (one who has been in close physical proximity). While this is harder to implement because it uses computationally expensive algorithms and needs a cryptographically secure random number generator in each device (both the implantable medical device 110, 210, 310, 404, 504, 604 and the external device 150, 250, 350, 402, 502, 602), the result is more robust, since the systems 100, 200, 300 and the methods 400, 500, 600 do not rely on the secrecy of the design or the lack of knowledge or skill of the attacker. The only known way to break the systems 100, 200, 300 and the methods 400, 500, 600 of the present subject matter is through an unfeasible amount of computation.

The present inventors have recognized various advantages of the subject matter described herein. The present inventors have recognized, among other things, that the present subject matter can be used to authorize an external device using physical proximity, eliminating the need to use biometric data or secret/fixed cryptographic keys. In various examples, the present subject matter is advantageous in that it provides quick and simple authentication by providing evidence of physical proximity over an insecure, short-range communication channel. In some examples, the present invention enables the system to use volatile keys, which can change from session to session, adding to the security of the system. In some examples, the present invention can provide authorization only once, when the external device provides evidence of physical proximity, so the present invention can still take advantage of a long-range communication channel after that, while maintaining the security benefits of short-range communication channel authentication. While various advantages of the example systems are listed herein, this list is not considered to be complete, as further advantages may become apparent from the description and figures presented herein.

Although the subject matter of the present patent application has been described with reference to various examples, workers skilled in the art will recognize that changes can be made in form and detail without departing from the scope of the subject matter recited in the below claims.

The above Detailed Description includes references to the accompanying drawings, which form a part of the Detailed Description. The drawings show, by way of illustration, specific examples in which the present apparatuses and methods can be practiced. These embodiments are also referred to herein as "examples."

The above Detailed Description is intended to be illustrative, and not restrictive. For example, the above-described examples (or one or more elements thereof) can be used in combination with each other. Other embodiments can be used, such as by one of ordinary skill in the art upon reviewing the above description. Also, various features or elements can be grouped together to streamline the disclosure. This should not be interpreted as intending that an unclaimed disclosed feature is essential to any claim. Rather, inventive subject matter can lie in less than all features of a particular disclosed embodiment. Thus, the following claims are hereby incorporated into the Detailed Description, with each claim standing on its own as a separate embodiment. The scope of the invention should be determined with reference to the appended claims, along with the full scope of equivalents to which such claims are entitled.

In this document, the terms "a" or "an" are used to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In this document, the terms "about" and "approximately" or similar are used to refer to an amount that is nearly, almost, or in the vicinity of being equal to a stated amount.

In the appended claims, the terms "including" and "in which" are used as the plain-English equivalents of the respective terms "comprising" and "wherein." Also, in the following claims, the terms "including" and "comprising" are open-ended, that is, an apparatus or method that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

The Abstract is provided to allow the reader to quickly ascertain the nature of the technical disclosure. It is submitted with the understanding that it will not be used to interpret or limit the scope or meaning of the claims.

The invention claimed is:

1. A method of establishing a communication session between an external device and an implantable medical device, the method comprising:
   generating a first private key, the first private key being generated by the external device;
   generating a first public key from the first private key, the first public key being generated by the external device;
   generating a second private key, the second private key being generated by the implantable medical device;
   generating a second public key from the second private key, the second public key being generated by the implantable medical device;

sending the second public key from the implantable medical device to the external device over a long-range communication channel;

generating a first shared key using the first public key and the second private key, the first shared key being generated by the implantable medical device and used by the implantable medical device to decrypt or encrypt one or more messages between the external device and the implantable medical device during the communication session; and generating a second shared key using the second public key and the first private key, the second shared key being generated by the external device and used by the external device to decrypt or encrypt one or more messages between the external device and the implantable medical device during the communication session.

2. The method of claim 1, comprising sending a start session order from the external device to the implantable medical device over the long-range communication channel.

3. The method of claim 2, wherein sending the start session order includes sending an authentication code from the external device to the implantable medical device over the long-range communication channel.

4. The method of claim 1, comprising sending evidence of physical proximity from the external device to the implantable medical device over a short-range communication channel.

5. The method of claim 4, wherein sending evidence of physical proximity includes sending an authentication code from the external device to the implantable medical device over the short-range communication channel.

6. The method of claim 1, wherein generating the first private key includes generating the first private key using a random number generator.

7. The method of claim 1, wherein generating the first public key from the first private key includes calculating the first public key from the first private key.

8. The method of claim 1, wherein generating the second public key from the second private key includes calculating the second public key from the second private key.

9. The method of claim 1, wherein generating the first and second shared keys includes generating the first shared key that is the same as the second shared key, the first and second keys being used in a block cipher algorithm for at least one of encryption and decryption of the one or more messages between the external device and the implantable medical device.

10. A method of establishing a communication session between an external device and an implantable medical device, the method comprising:

generating a first private key, the first private key being generated by the external device;

generating a first public key from the first private key, the first public key being generated by the external device;

generating a second private key, the second private key being generated by the implantable medical device;

generating a second public key from the second private key, the second public key being generated by the implantable medical device;

sending the second public key from the implantable medical device to the external device over a long-range communication channel;

generating a first shared key using the first public key and the second private key, the first shared key being generated by the implantable medical device; and generating a second shared key using the second public key and the first private key, the second shared key being generated by the external device, wherein the first shared key is the same as the second shared key, the first and second keys being used in a block cipher algorithm for at least one of encryption and decryption of the one or more messages between the external device and the implantable medical device during the communication session.

11. The method of claim 10, comprising sending a start session order from the external device to the implantable medical device over the long-range communication channel.

12. The method of claim 11, comprising sending evidence of physical proximity from the external device to the implantable medical device over a short-range communication channel.

13. The method of claim 12, wherein sending the start session order includes sending an authentication code from the external device to the implantable medical device over the long-range communication channel.

14. The method of claim 13, wherein sending evidence of physical proximity includes sending the authentication code from the external device to the implantable medical device over the short-range communication channel.

15. The method of claim 14, comprising:

comparing the authentication code received by the implantable medical device over the short-range communication channel to the authentication code received by the implantable medical device over the long-range communication channel; and aborting the establishing of the communication session if the authentication code received by the implantable medical device over the short-range communication channel is not the same as the authentication code received by the implantable medical device over the long-range communication channel.

16. The method of claim 10, wherein:

generating the first and second private keys includes generating the first and second private keys using a random number generator; and generating the first and second public keys from the first and second private keys, respectively, includes calculating the first and second public keys from the first and second private keys, respectively.

17. A method of establishing a communication session between an external device and an implantable medical device, the method comprising:

generating a first private key, the first private key being generated by the external device;

generating a first public key from the first private key, the first public key being generated by the external device;

sending a start session order from the external device to the implantable medical device over a long-range communication channel;

sending evidence of physical proximity from the external device to the implantable medical device over a short-range communication channel;

generating a second private key, the second private key being generated by the implantable medical device;

generating a second public key from the second private key, the second public key being generated by the implantable medical device;

sending the second public key from the implantable medical device to the external device over the long-range communication channel;

generating a first shared key using the first public key and the second private key, the first shared key being generated by the implantable medical device and used by the implantable medical device to decrypt or encrypt one or more messages between the external device and the implantable medical device during the communication session; and generating a second shared key using the second public key and the first private key, the second shared key being generated by the external device and used by the external device to decrypt or encrypt one or more messages between the external device and the implantable medical device during the communication session.

18. The method of claim 17, wherein generating the first and second shared keys includes the first shared key being the same as the second shared key, the first and second keys being used in a block cipher algorithm for at least one of encryption and decryption of the one or more messages between the external device and the implantable medical device during the communication session.

19. The method of claim 18, comprising:

sending an authentication code from the external device to the implantable medical device over the long-range communication channel;

sending the authentication code from the external device to the implantable medical device over the short-range communication channel;

comparing the authentication code received by the implantable medical device over the short-range communication channel to the authentication code received by the implantable medical device over the long-range communication channel; and aborting the establishing of the communication session if the authentication code received by the implantable medical device over the short-range communication channel is not the same as the authentication code received by the implantable medical device over the long-range communication channel.

20. The method of claim 17, wherein:

generating the first and second private keys includes generating the first and second private keys using a random number generator; and generating the first and second public keys from the first and second private keys, respectively, includes calculating the first and second public keys from the first and second private keys, respectively.

* * * * *